(12) United States Patent
Claude (10) Patent No.: US 12,011,591 B2
(45) Date of Patent: Jun. 18, 2024

(54) TRANSCRANIAL ALTERNATING CURRENT DYNAMIC FREQUENCY STIMULATION (TACS) METHOD FOR ALZHEIMERS AND DEMENTIA

(71) Applicant: Nexalin Technology, Inc., Houston, TX (US)

(72) Inventor: John Patrick Claude, Redwood City, CA (US)

(73) Assignee: NEXALIN TECHNOLOGY, INC., Houston, TX (US)

( * ) Notice: Subject to any disclaimer, the term of this patent is extended or adjusted under 35 U.S.C. 154(b) by 0 days.

(21) Appl. No.: 18/342,590

(22) Filed: Jun. 27, 2023

(65) Prior Publication Data

US 2023/0381510 A1    Nov. 30, 2023

Related U.S. Application Data (62) Division of application No. 17/116,233, filed on Dec. 9, 2020, now Pat. No. 11,872,397.

(Continued)

(51) Int. Cl.
*A61N 1/36* (2006.01)

(52) U.S. Cl.
CPC ..... *A61N 1/36025* (2013.01); *A61N 1/36034* (2017.08)

(58) Field of Classification Search
CPC ............ A61N 1/36025; A61N 1/36034; A61N 1/36031; A61N 1/36082; A61N 1/0456; A61N 1/3603

See application file for complete search history.

(56) References Cited

U.S. PATENT DOCUMENTS

| 5,540,736 A | 7/1996 | Haimovich |
| 6,904,322 B2 | 6/2005 | Katsnelson |

(Continued)

FOREIGN PATENT DOCUMENTS

| WO | WO2020041633 | 2/2020 |
| WO | WO2021102447 | 5/2021 |

OTHER PUBLICATIONS

Artikis, T.; European Search Report; Mar. 18, 2024; 7 pages; Munich, Germany.

(Continued)

*Primary Examiner* — Amanda K Hulbert
*Assistant Examiner* — Natasha Patel
(74) *Attorney, Agent, or Firm* — STETINA BRUNDA GARRED & BRUCKER (57) ABSTRACT

Transcranial electrostimulation systems and methods are contemplated in which a high current level, charge balanced alternating current electrical signal is generated for delivery to the occipital region of a patient's brain. By stimulating the brain with a charged balanced stimulation current with a stimulation current envelope defining one or more series of pulses at particular frequencies and durations designed to evoke metabolic response in the neurons, significant improvements in efficacy and reductions in patient discomfort may be achieved relative to earlier methods of transcranial electrical stimulation, especially those in which result in a resultant rectified direct current component being administered to the patient. Further advantages, especially in promoting neural entrainment, may be realized as well via utilizing multiple series of pulses at different frequencies, and via the dynamic adjustment of the stimulation waveform via incorporation of feedback signals in order to maintain charge balance in real-time.

20 Claims, 6 Drawing Sheets

Related U.S. Application Data (60) Provisional application No. 63/061,255, filed on Aug. 5, 2020, provisional application No. 63/054,964, filed on Jul. 22, 2020.

(56) References Cited

U.S. PATENT DOCUMENTS

| | | |
|---|---|---|
| 7,742,823 B2 | 6/2010 | King et al. |
| 7,769,463 B2 | 8/2010 | Katsnelson |
| 9,227,056 B1 | 1/2016 | Heldman et al. |
| 10,543,367 B2 | 1/2020 | Peng et al. |
| 2002/0177882 A1 | 11/2002 | DiLorenzo |
| 2006/0015153 A1 | 1/2006 | Gliner et al. |
| 2008/0319492 A1 | 12/2008 | Katsnelson |
| 2009/0149898 A1 | 6/2009 | Hulvershorn et al. |
| 2012/0310298 A1 | 12/2012 | Besio et al. |
| 2015/0238759 A1* | 8/2015 | Katsnelson ........ A61N 1/36034 607/66 |
| 2015/0328467 A1 | 11/2015 | Demers |
| 2016/0175585 A1 | 6/2016 | Gregory et al. |
| 2016/0206883 A1 | 7/2016 | Bornzin et al. |
| 2016/0346530 A1 | 12/2016 | Jeffery et al. |
| 2017/0296121 A1 | 10/2017 | Dar et al. |
| 2019/0022372 A1 | 1/2019 | Dar et al. |
| 2019/0209841 A1 | 7/2019 | Errico et al. |
| 2020/0023189 A1 | 1/2020 | Gribetz et al. |
| 2020/0038656 A1 | 2/2020 | Tyler et al. |
| 2021/0038892 A1 | 2/2021 | Velasco Valcke |
| 2022/0160995 A1 | 5/2022 | Wetmore et al. |

OTHER PUBLICATIONS

Rodriquez, Kari; PCT International Search Report; Sep. 27, 2021; 9 pages; Alexandria, Virginia.

Rodriquez, Kari; PCT International Search Report; Oct. 25, 2021; 18 pages; Alexandria, Virginia.

* cited by examiner

TRANSCRANIAL ALTERNATING CURRENT DYNAMIC FREQUENCY STIMULATION (TACS) METHOD FOR ALZHEIMERS AND DEMENTIA

CROSS-REFERENCE TO RELATED APPLICATIONS

This is a divisional application of U.S. Ser. No. 17/116,233 filed on Dec. 9, 2020 and entitled "TRANSCRANIAL ALTERNATING CURRENT DYNAMIC FREQUENCY STIMULATION (TACS) SYSTEM AND METHOD FOR ALZHEIMERS AND DEMENTIA" and relates to and claims the benefit of U.S. Provisional Application No. 63/054,964 filed Jul. 22, 2020 and entitled "TRANSCRANIAL ALTERNATING CURRENT DYNAMIC FREQUENCY STIMULATION (TACS) SYSTEM AND METHOD FOR ALZHEIMERS AND DEMENTIA" the entire disclosure of which is hereby wholly incorporated by reference, and this application relates to and claims the benefit of U.S. Provisional Application No. 63/061,255 filed Aug. 5, 2020 and entitled "TRANSCRANIAL ALTERNATING CURRENT DYNAMIC FREQUENCY STIMULATION (TACS) SYSTEM AND METHOD FOR ALZHEIMERS AND DEMENTIA" the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to the field of transcranial electrostimulation. More particularly, the present disclosure relates to improved systems and methods for transcranial electrostimulation for treating Alzheimer's Dementia and other dementia diseases.

2. Related Art

Electrostimulation devices for applying current to a patient through electrodes located on the head have been developed and used for a variety of purposes in the past, such as for producing analgesic effects, inducing sleep, and reducing or controlling migraine headaches. Generally, such treatments are referred to as transcranial electrostimulation (TCES) or cranial electrostimulation (CES). Conventional TCES devices, although employed for a number of different purposes, may have severe drawbacks. For example, many conventional TCES devices utilize a direct current (DC) component in order to break down or lower the resistance of the skin and to allow the treatment current (which may a combination of direct and alternating current) to penetrate to the nervous system.

The presence of a DC component of a treatment current produced by a TCES device generally results in an unpleasant experience for a patient undergoing TCES therapy. In early TCES designs, the presence of the DC current invariably would result in intense pain or burns to the skin of the wearer, requiring the placement of thick conductive padding between the electrodes and the skin of the wearer in order to render the treatment bearable. Even in more recently developed TCES therapies in which the levels of DC current are limited, these limited amounts of DC current still often result in substantial user discomfort. Additionally, even when only an alternating current is applied to the skin, the layers of the skin generally result in a non-linear, complex impedance that invariably rectifies the AC signal and generates a DC component. This DC component depolarizes nociceptors in the skin, causing discomfort in the patient. If the DC-stimulated nociceptors are efferent to a trigeminal nerve branch in the head, the discomfort may be protected into the forehead region.

This patient discomfort resulting from DC rectification presents an upper limit on the amount of power that can be delivered even in an AC-only TCES therapy. Because of this upper limit on power, such conventional therapies are limited in their efficacy. This is especially pronounced when it may be desired to utilized TCES therapy to treat Dementia diseases such as Alzheimer's Dementia, where the amount of power delivered may be insufficient to penetrate into the deep structures in the brain associated with early Dementia and loss of memory and cognition.

Therefore, novel systems and methods for transcranial electrostimulation are desirable.

BRIEF SUMMARY

To solve these and other problems, novel systems and methods for treating a patient for Alzheimer's Dementia (AD) are contemplated in which a transcranial electrostimulation system produces a high current level, dual symmetric charge balanced alternating current electrical signal for delivery to the occipital region of a patient's brain. By stimulating the brain with a charged balanced AC stimulation current having a stimulation current envelope defining a series of pulses having a particular frequency, with the stimulation current being delivered for a particular duration, together designed to evoke particular metabolic responses in the neurons, significant improvements in efficacy and reductions in patient discomfort may be achieved relative to earlier methods of transcranial electrical stimulation, especially those in which a direct current or a resultant rectified direct current component is administered to the patient. Further advantages, especially in promoting neural entrainment, may be realized as well via delivery of the charged-balanced stimulation current such that its envelope defines multiple series of pulses at different frequencies, and via the dynamic alteration of the stimulation current via incorporation of feedback signals in order to maintain charge balance in real-time, in order to maintain charge balance.

Transcranial electrostimulation systems for treating a patient for Alzheimer's Dementia are contemplated which may comprise a carrier waveform generator, a stimulation current generator, and a patient cable. A stimulation current may be generated from a carrier waveform output from the carrier waveform generator, with the carrier waveform being an alternating current having a duty cycle ratio and a current amplitude ratio, the duty cycle ratio and the current amplitude ratio being selected such that each respective integration of the current amplitude between successive time instances at which the carrier waveform alternates polarity is substantially equivalent. The stimulation current may be subsequently conveyed to the patient via the patient cable.

The contemplated transcranial electrostimulation systems for treating a patient for Alzheimer's Dementia may further be configured to amplitude modulate the carrier waveform prior during the process of generating the stimulation current, such that the extremes of the stimulation current define a stimulation current envelope. The stimulation current envelope may further be amplitude modulated such that the stimulation current envelope defines a first series of pulses occurring at a first frequency. The frequency of the first series of pulses may be about 40 Hz.

The contemplated transcranial electrostimulation systems for treating a patient for Alzheimer's Dementia may further be configured to generate a stimulation current wherein the stimulation current envelope further defines a second series of pulses occurring at a second frequency. According to certain exemplary embodiments, the second series of pulses may occur at a frequency selected from: about 4 Hz, about 40 Hz, about 77.5 Hz.

The contemplated transcranial electrostimulation systems for treating a patient for Alzheimer's Dementia may further be configured such that the stimulation current is conveyed to the patient for a treatment duration, with the stimulation current defining a stimulation current envelope, the stimulation current envelope defining a first series of pulses that occur at a frequency of about 40 Hz for the entire treatment duration, and defining a second series of pulses that occur at a frequency of about 4 Hz for a first portion of the treatment duration, a frequency of about 40 Hz for a second portion of the treatment duration, and a frequency of about 77.5 Hz for a third portion of the treatment duration. The treatment duration may be, for example, about an hour, with each of the first portion of the treatment duration, the second portion of the treatment duration, and the third portion of the treatment duration being about minutes.

According to various further refinements of the contemplated transcranial electrostimulation systems, the stimulation current may be configured such that it defines a stimulation current envelope which itself defines a plurality of series of pulses, each respective one of the plurality of series of pulses occurring at a respective frequency. In even further refinements of the above concept, each of the plurality of series of pulses defined by the stimulation current envelopes has a frequency selected from one or more of: about 4 Hz, about Hz, about 77.5 Hz.

The transcranial electro stimulation systems for treating a patient for Alzheimer's Dementia may further be configured such that the carrier waveform may have a frequency of about 100 KHz, such that the carrier waveform is a rectangular wave, or both.

According to various further refinements of the contemplated transcranial electrostimulation systems, the system(s) may further comprise one or more reference electrodes, the stimulation current being measured at the patient by the one or more reference electrodes and an electrode contact impedance being determined therefrom, and a controller in communication with the one or more reference electrodes, the controller adjusting, based upon the determined electrode contact impedance, one or more parameters of: the carrier waveform output from the waveform generator, the stimulation current output from the stimulation current generator, or combinations thereof.

Methods for treating a patient for Alzheimer's Dementia are also contemplated, with such methods comprising the steps of: (a) generating a carrier waveform, the carrier waveform being an alternating current having a duty cycle ratio and a current amplitude ratio, the first duty cycle ratio and the first current amplitude ratio being selected such that each respective integration of the current amplitude between successive time instances at which the first waveform alternates polarity is substantially equivalent; and generating a stimulation current from the carrier waveform via amplitude modulation the carrier waveform, the extremes of the stimulation current defining a stimulation current envelope, the stimulation current envelope defining a first series of pulses occurring at a first frequency; and (b) applying the stimulation current to the occipital region of the brain of the patient. According to the particular refinements of such methods, the first series of pulses may occur at a frequency of about 40 Hz.

The step of generating a stimulation current may, in additional embodiments, occur via amplitude modulating the carrier waveform such that the stimulation current envelope current further defines a second series of pulses occurring at a second frequency. The frequency of the second series of pulses may be selected from, for example, about 4 Hz, about 40 Hz, or about 77.5 Hz.

The above described methods may also comprise applying the stimulation current to the occipital region of the brain of a to a patient for a treatment duration, wherein the first series of pulses occur at a frequency of about 40 Hz for the entire treatment duration, and wherein the second series of pulses occur at a frequency of about 4 Hz for a first portion of the treatment duration, a frequency of about 40 Hz for a second portion of the treatment duration, and a frequency of about 77.5 Hz for a third portion of the treatment duration. The treatment duration may be, for example, an hour, with each of the first portion of the treatment duration, the second portion of the treatment duration, and their third portion of the treatment duration being about 20 minutes.

According to further refinements of the above described methods, the step of generating the stimulation current may be performed via amplitude modulating the carrier waveform such that the stimulation current envelope defines a plurality of series of pulses, each respective one of the plurality of series of pulses occurring at a respective frequency. Such frequencies may be selected from one or more of: about 4 Hz, about 40 Hz, about 77.5 Hz. Further, it is contemplated that the carrier waveform may have a frequency of about 100 KHz, may be a rectangular wave, or both.

In further refinements of the above described methods, additional steps may be included such as: measuring the stimulation current at the patient, determining of an electrode contact impedance therefrom, and based upon the determined electrode contact impedance, adjusting one or more of: the waveform output from the waveform generator, the stimulation current output from the stimulation current generator, or combinations thereof.

A method of generating a stimulation current is also contemplated, with the method comprising generating a carrier waveform, the carrier waveform being a rectangular alternating current having a duty cycle ratio and a current amplitude ratio, the duty cycle ratio and the current amplitude ratio being selected such that each respective integration of the current amplitude between successive time instances at which the waveform alternates polarity is substantially equivalent, and amplitude modulating the carrier waveform to derive a stimulation current, the extreme of the stimulation current defining a stimulation current envelope, the stimulation current envelope defining a first series of pulses occurring at a first frequency.

DETAILED DESCRIPTION

According to various aspects of the present disclosure, new systems and methods for transcranial electrostimulation (TCES) are contemplated in which a "symmetric" or charge balanced AC signal is delivered to the patient in a manner that permits higher levels of overall power to be transmitted more deeply into the brain without the limitations of the patent discomfort threshold, permitting evocation of nerves in the deep brain structures and enhancing treatment outcome. This increase in power may enhance treatment efficacy and response without any adverse clinical sequelae. By amplitude modulating the carrier waveform to incorporating a blend of multiple frequency patterns of the series of pulses defined by the stimulation current envelope into the treatment, such as a first frequency pattern at 40 Hz for an entire one hour treatment duration, and a second frequency pattern in a sequence of 4 Hz, 40 Hz, and 77.5 Hz for 20 minutes each, the blended frequency pattern of the stimulation current envelope may result in metabolic cleansing and regeneration in damaged neurons, which in particular may be seen to reduce and possibly reverse the symptoms associated with dementia diseases such as Alzheimer's Dementia (AD).

Figure 1:
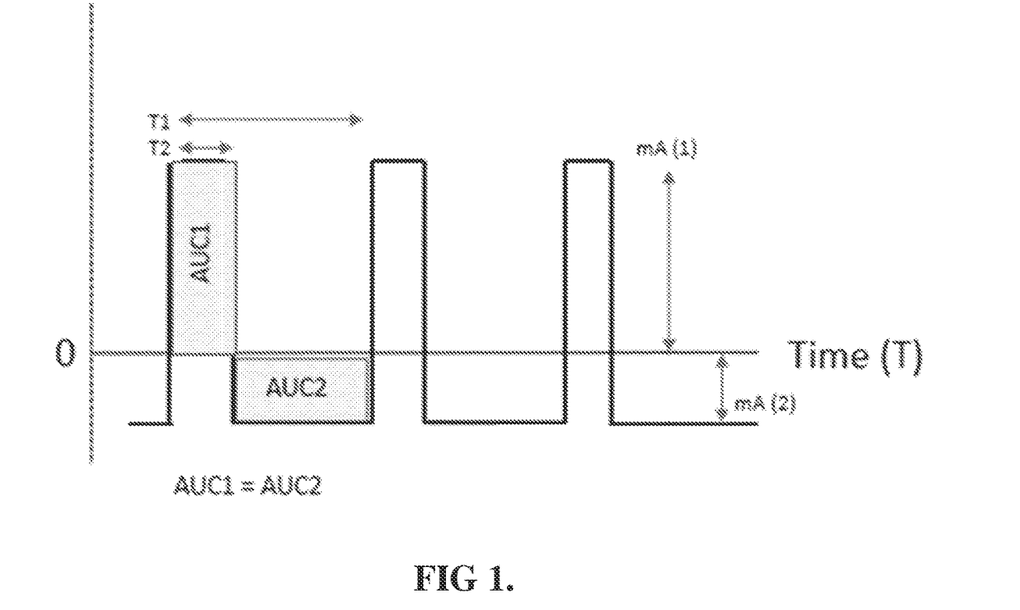
FIG. 1 is an illustration showing an embodiment of a high frequency (100 KHz) rectangular alternating current carrier waveform that is charge-balanced, in that the area under the curves (AUC) for each respective integration of current amplitude between successive time instances at which the carrier alternates polarity is equal, with such charge balance resulting from the choice of a particular duty cycle ratio (T2:T1) and a particular current amplitude ratio (Ma(1):Ma (2)) for the carrier waveform.

Turning now to FIG. 1, an exemplary embodiment of a rectangular alternating current (AC) carrier waveform is illustrated. As may be seen, the exemplary rectangular AC carrier waveform has, between each successive alternation of polarity, an area under the curve (AUC), i.e., the integration of the current amplitude between successive time instances at which the waveform alternates polarity. For the waveform to be "symmetric" or "change balanced," each successive pair of AUC between polarity shifts in the AC waveform must be equal. Via the original rectangular AC carrier waveform being charged balanced in this fashion, it may be seen that the ultimate stimulation current derived from amplitude modulating this waveform will not result in undesired rectification when applied to the patient's skin and thus will not result in the production of a DC component that will cause discomfort or pain in the patient.

The carrier waveform itself may be any type of alternating current waveform. In the exemplary embodiment of FIG. 1, it may be seen that the waveform is generally in the form of a rectangular wave. However, it may be seen that other waveform types may be used as carrier waveforms, such as sinusoidal or triangular waves. It may also be seen that this charge balancing, wherein the AUC of each successive pair of regions between alternation in polarity are substantially equivalent, may be achieved in a variety of ways, such that each respective pair of waveforms is not necessarily required to have the same geometry as those preceding it. As shown in the image, the "on" positive amperage portions of the illustrated carrier waveform have a greater magnitude than the "off" negative amplitude portions, but are of a shorter duration (T2), with the duration of the "off" negative amperage portions of the carrier waveform being longer (T1-T2) and with a lesser magnitude. This ratio of the time when the carrier waveform "on" versus "off" is referred to as the duty cycle ratio, which is calculated here, when a rectangular AC waveform is used as the carrier wave, as (T2)/(T1). It may be seen that by controlling the relative magnitudes of the amperages, durations, and possibly even the shape itself of the carrier waveform or portions thereof (especially in non-square waveforms), a carrier waveform may be achieved that is charge balanced. Thus it may be seen that in the case of a dynamic signal, when the duty cycle ratio (T2/T1) of the waveform is changed, so must the current amplitude ratio (mA(1)/mA(2)) also be changed to compensate and maintain the charge balanced nature of the waveform in order to prevent the ultimate stimulation current produced from producing a rectified DC component at the patients' skin when applied to the patient. For example, with a rectangular waveform, the following Table 1 shows various duty cycles and corresponding carrier amplitude ratio pairings that will result in a charge balanced waveform:

TABLE 1

Charged Balanced Duty Cycle Ratio and Current Amplitude Ratio Pairings

| Duty Cycle Ratio | Current Amplitude Ratio |
| --- | --- |
| 1:3 | 2:1 |
| 1:4 | 3:1 |
| 1:5 | 4:1 |

In the exemplary embodiment, the carrier waveform is a high-frequency rectangular alternating current, which has a frequency of about 100 KHz. It has generally been found that use high frequency carrier waveform is most beneficial for permitting deep penetration of the stimulation current into targeted regions of the patient's brain. However, in other embodiments, it is contemplated that higher or lower frequencies than 100 KHz may be utilized, without departing from the scope and spirt of the present disclosure. Likewise, it may also be seen that variation in the frequency of the carrier waveform over time or in response to stimuli or other inputs may be utilized in order to enhance the functionality of the transcranial electrostimulation device.

Figure 2:
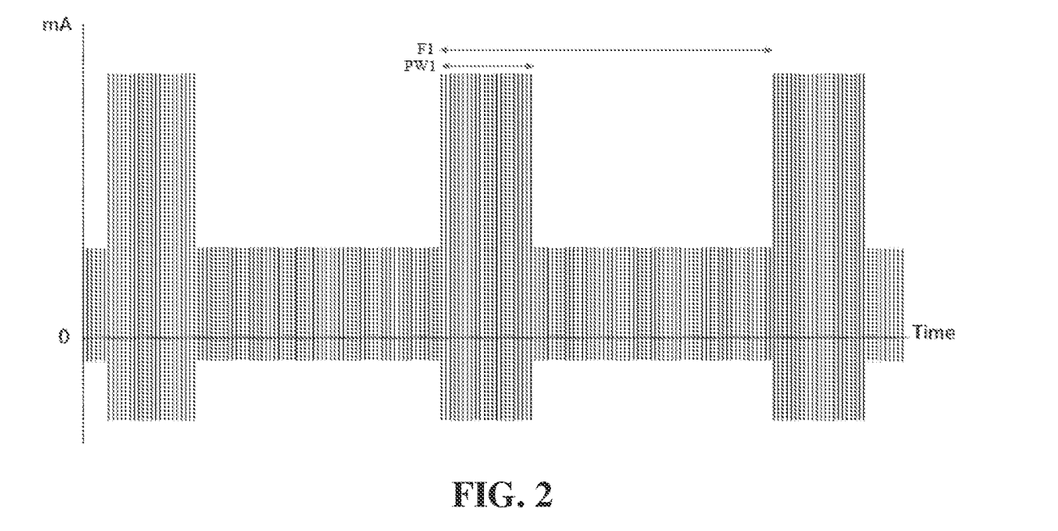
FIG. 2 is an illustration showing one embodiment of stimulation current comprising the result of amplitude modulating the carrier waveform of FIG. 1 such that the extremes of the stimulation current define a stimulation current envelope, with the stimulation current envelope defining a first series of pulses occurring at a frequency F1 and having a pulse width PW1.

Turning now to FIG. 2, an exemplary embodiment of a stimulation current that has been produced via amplitude modulation of the high frequency carrier waveform of FIG. 1 is illustrated. As may be seen, the extremes of the amplitude modulated high frequency carrier waveform define a stimulation current envelope, which results as a consequence of the particular parameters of the amplitude modulation. The stimulation current envelope may itself be seen to define a first series of pulses occurring at a first frequency F1 and having a pulse width PW2. When applied to the occipital region of the patient's brain, the stimulation current may induce neural entrainment, causing neurons within the patient's brain to be stimulated via a polarization of the electrical charge on the outside of the membrane in accordance with the frequency of the first series of pulses. As long as the magnitude and pulse width of the pulses defined by the stimulation current envelope are sufficient to promote neural stimulation and trigger an action potential, and as long as the frequency of the series of pulses are not too high so as to permit the neuron to complete its refractory period prior to excitation via the subsequent pulse, neural entrainment may occur at the neurons that are affected by the stimulation current.

Figure 3:
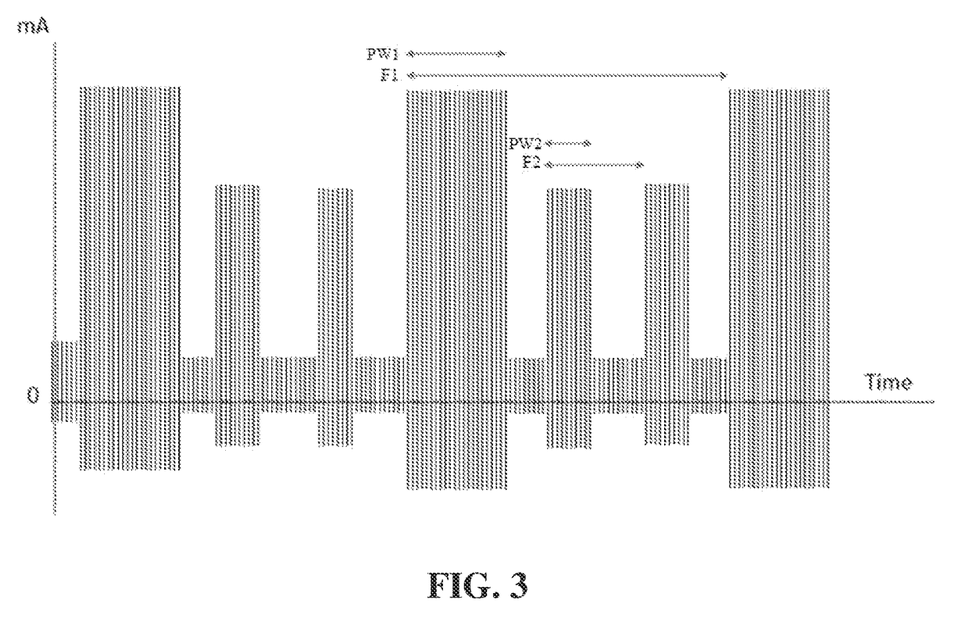
FIG. 3 is an illustration showing another embodiment of a stimulation current comprising the result of amplitude modulating the carrier waveform of FIG. 1 such that the extremes of the stimulation current define a stimulation current envelope, with the stimulation current envelope defining a first series of pulses occurring at a frequency F1 and having a pulse width PW1, and defining a second series of pulses occurring at frequency F2 and having a pulse width PW2.

Turning now to FIG. 3, another exemplary embodiment of a stimulation current is illustrated in which the original carrier waveform shown in FIG. 1 has been amplitude modulated such that a first and a second series of pulses are defined by the stimulation current envelope, the first series of pulses having a frequency F1 and a pulse width PW1, and the second series of pulses having a frequency F2 and a pulse width PW2. It may be seen that in this embodiment, the second series of pulses occur at a higher frequency (F2), have a shorter pulse width, and are of a lesser magnitude than the pulses within the first series of pulses. However, it may be seen that in other embodiments of stimulation currents, the pulses of one series of pulses may have higher or lower frequencies, shorter or longer pulse widths, and greater or lesser magnitudes than the pulses of another series of pulses, without departing from the scope and spirit of the presently contemplating disclosure. In this manner, it may be seen that such a stimulation current defining an envelope with multiple series pulses may be created. As a result, by optimizing the parameters of the pulses of each series of pulses, neural entrainment of certain neurons within the patient's brain may be facilitated at Frequencies F1 and/or F1 when the stimulation current is delivered to the patient, with the stimulating current still being charge balanced and not resulting in substantial patient discomfort. By, for example, configuring the stimulation current to have different pulse widths or amplitudes for certain of the series of pulses, it may be seen that certain types or regions of neurons may be targeted by some of the series of pulses for neural entrainment, while other types or regions of neurons may be targeted by others of the series of pulses for neural entrainment.

It may also be seen that other types of schemes for creating a combined stimulation current envelope having other features may be utilized, such as those in which the stimulation current is generated in which the stimulation current envelope defines three or more series of pulses, each series of pulses which may have different parameters in order to facilitate neural entrainment of different types of neurons, or in which the frequencies of the series of pulses defined by the stimulation current envelope are adjustable or configured to adjust according to the receipt of or other feedback, stimuli, or other inputs at the transcranial electrostimulation device.

According to certain exemplary embodiments, in particular it has been discovered that by administering a charge balanced stimulation current which contains a blend of different frequency patterns, neuronal responses within a patient's brain may be evoked which may tend to result in metabolic cleansing and regeneration in damaged neurons. Notably, it is contemplated that administration of a charged balanced stimulation current having a stimulation current envelope that defines a first series of pulses occurring at a 4 Hz frequency, when delivered to the patient, may tend to evoke a metabolic cleansing response. It has also been discovered that the definition by the stimulation current envelope of a second series of pulses occurring at a 40 Hz frequency, when delivered to the patient, may tend to promote a neuronal regenerative response. Thus, it is contemplated that a stimulation current having a stimulation current envelope that defines both a 4 Hz first series of pulses and a 40 Hz second series of pulses may be delivered to a patient in order to achieve both of these results. Further, it is contemplated that by varying the frequency least one of the two series of pulses over time during the administration of a treatment regimen, a synergistic beneficial effect may be realized as a result of the different neural entrainment outcomes resulting from the particular choices used. For example, in one particular embodiment, the stimulation current may have a stimulation current envelope defining a first series of pulses occurring at a constant 40 Hz frequency for the entire duration of the treatment, with the stimulation current envelope also defining a second series of pulses occurring at a variable frequency, the variable frequency being 4 Hz for a first portion of the treatment, 40 Hz for a second portion of the treatment, and 77.5 Hz for a third portion of the treatment. It is further contemplated that for a treatment with a duration of an hour, each of the first, second, and third portions of treatment may be roughly equal, i.e., be 20 minutes in length. As such, the transcranial electrostimulation device may be configured to output a stimulation current according to these parameters. It may also be seen that via the delivery of a stimulation current having different frequency and amplitude patterns characteristics of its combined stimulation current envelope, multiple different neural regions may be configured to be stimulated in various ways across a single course of treatment, according to the effects desired to be achieved via such stimulation treatment regimens.

Figure 4:
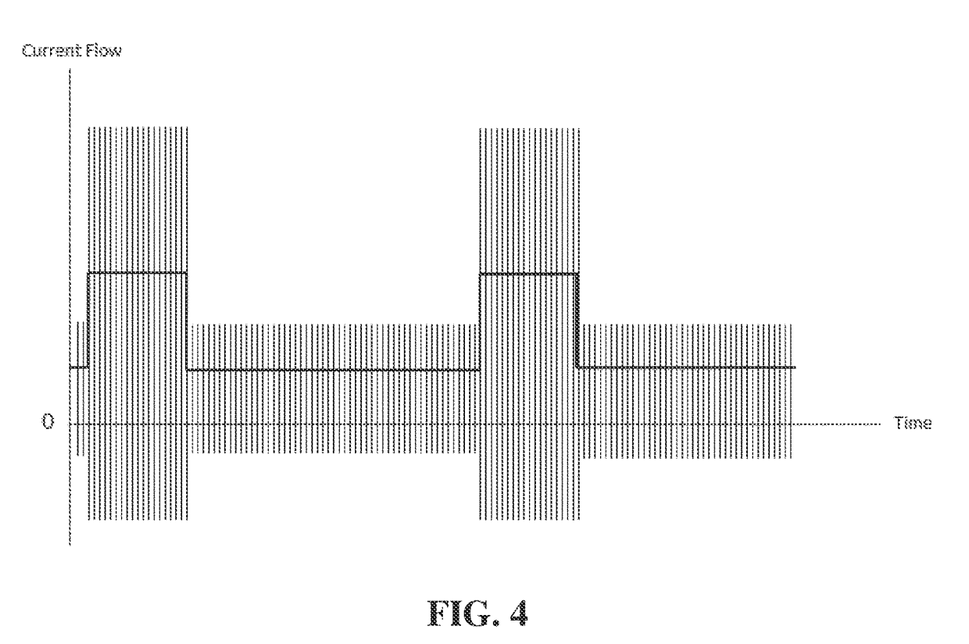
FIG. 4 is an illustration showing an example of a resultant rectified charge that is entrained at the neurons within the occipital region of a patient's brain, overlaid atop the example of the stimulation current shown in FIG. 2, the resultant rectified charge occurring as a consequence of transcranial application of the illustrated stimulation current to occipital region of a patient's brain.

Turning now to FIG. 4, an example of a resultant rectified charge that is entrained at the neurons within the occipital region of a patient's brain as a result of delivery of an exemplary stimulation current to the occipital region of the patient's brain is shown overlaid atop that exemplary stimulation current. It may be seen that this resultant rectified charge may occur as a consequence of transcranial application of the illustrated stimulation current to occipital region of a patient's brain, which causes this rectified charge to accrue at the neurons. This rectified charge accrual results in polarization of the electrical charge on the outside of the neural membrane, in accordance with the frequency of the first series of pulses defined by the envelope of the stimulation current. As long as the magnitude and pulse width of the pulses defined by the stimulation current envelope are sufficient to cause sufficient accrual of electrical charge at a neuron to elevate the resting potential of the neuron to the threshold of excitation, an action potential of the neuron will be triggered. As may be seen, a higher magnitude pulse of a lesser pulse width may be sufficient to cause enough charge to accrue, or a lower magnitude pule of a greater pulse width may be sufficient, so long as the sufficient voltage is achieved at the membrane of the neuron as a result of delivery of the stimulation current. Further, it may be seen that so long as the frequency of the series of pulses are not too high (i.e., longer than the neuronal refractory period) each pulse will separate trigger another action potential within the neuron in order to cause natural entrainment to the frequency of the first series pulses. It may further be seen, however, that configurations of the different parameters of stimulation currents may result in some pulses being received at some neurons prior to the recovery of the neuronal refractory period resulting from triggering of the action potential by an earlier pulse. Such schemes may be utilized in order to, for example, target entrainment of certain types or localities of neurons according to a first frequency, and to target entrainment of another type or locality of neurons according to a second frequency.

Figure 5:
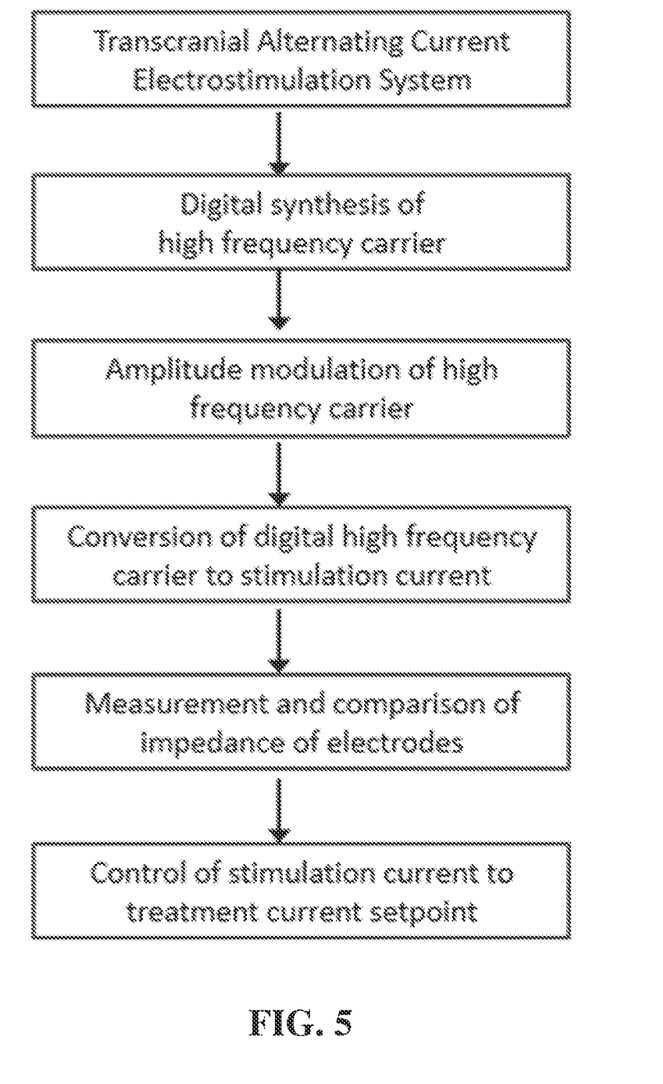
FIG. 5 is a flowchart showing certain steps of an embodiment of a method for treating a patient for Alzheimer's Dementia.

Turning now to FIG. 5, a flowchart showing certain steps of an embodiment of a method for treating a patient for Alzheimer's Dementia via the dynamic delivering a charge balanced alternating current electrical signal to the occipital region of a patient's brain is shown. In particular, it is contemplated that a TCES system may first digitally synthesize one or more high frequency rectangular AC carrier waveforms, which may or may not be similar to the waveform illustrated in FIG. 1. The TCES system may then amplitude modulate the high frequency carrier waveform, as described in detail above, according to the particular parameters ultimately desired in the stimulation current, ultimately producing a stimulation current, which will then be conveyed to the patient. It is further contemplated that in certain embodiments, a measurement of electrode contact impedance may be taken at the patient at the point of delivery of the stimulation current via one or more reference electrodes. In these embodiments, the stimulation current may then be controlled (such as via alternation of the parameters of the high frequency carrier waveform, or by alteration of the various factors of the amplitude modulation) in order to better optimize the performance of the stimulation current, to confirm electrode contact quality, and to prevent any current imbalances that may result in unequal stimulation or inadvertent generation of DC components that may result in discomfort to the patient.

Figure 6:
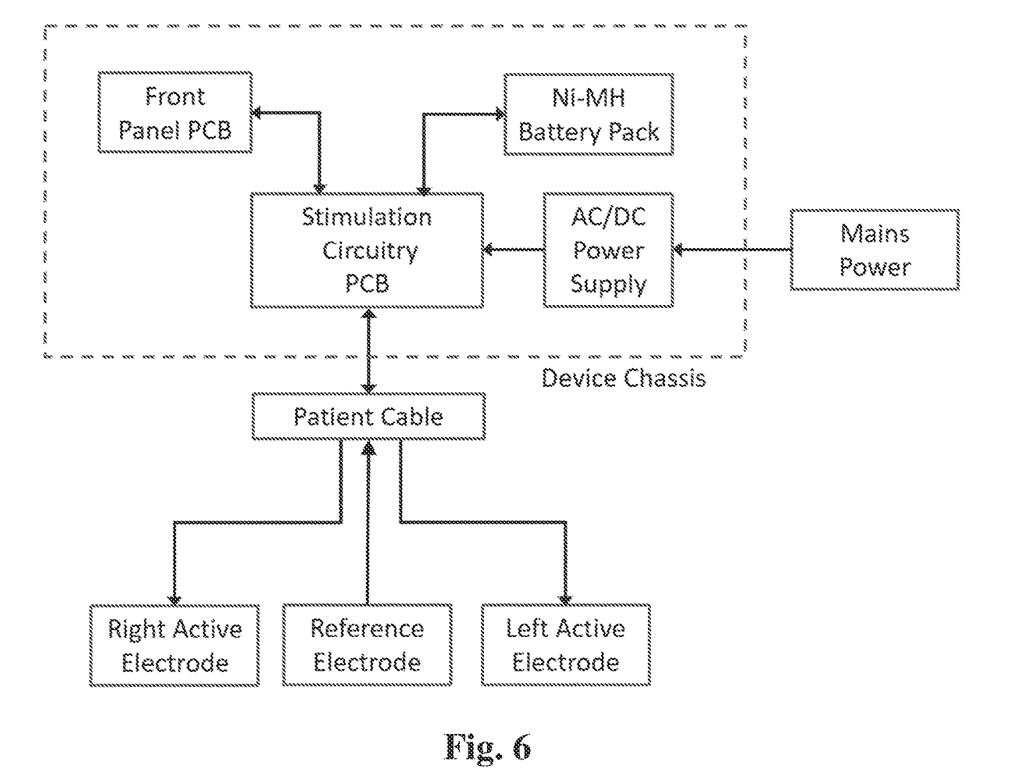
FIG. 6 is a block diagram showing certain hardware components of an embodiment of a transcranial electrostimulation system for treating a patient for Alzheimer's Dementia.

Turning now to FIG. 6, a block diagram of an exemplary Transcranial Alternating Current Dynamic Frequency Stimulation (TACS) system is illustrated. As may be seen, one exemplary embodiment of a TACS system may comprise a device chassis containing an AC/DC power supply, a stimulation circuitry printed circuit board (PCB), a front panel PCB, and a battery pack, configured for use with an external mains power source that feeds into the AC/DC power supply. Also included is a patient cable for conveying the stimulation current to the patient may be attached to the stimulation circuitry PCB, with the patient cable having a right active electrode, a left active electrode, and a reference electrode. While this specific block diagram shows one exemplary version of a TACS system, it is certainly not the only configuration in which the systems and methods herein described may be achieved, and indeed, these descriptions of the actual physical architecture of a TACS system are to be understood as being purely for exemplary purposes in order to enable the reader to more fully understand the nature of the herein described systems and methods, and are not to be interpreted as representing or imposing any limitations of the subject matter described herein. For example, but without limitation, it may not be necessary for some or all components to be contained within a physical device chassis, or for many of these components to be present in the exact form described or at all.

The stimulation circuitry PCB may be for controlling the functionality of the TACS related to the generation and control of the stimulation current, including the synthesis of a high frequency carrier waveform. In this respect, it is to be understood as including as subsidiary components (which may be hardware or software components, or combinations thereof) both the waveform generator and the stimulation current generator. The stimulation circuitry PCB will be more fully described in relation to the foregoing discussion of FIG. 7.

The front panel PCB may be for supporting the user interface for the TACS system, and may include, for example, means for user input and for display of information to the user. The front panel PCB will be more fully described in relation to the foregoing discussion of FIG. 8.

The patient cable may be for conveying the stimulation current produced at the TACS to the patient. The patient cable may include or be connected to two or more active electrodes for delivering the stimulation current to the patient, and may further include or be connected to one or more reference electrodes for determining stimulation output voltage and returning measurements which will be used to determine electrode impedance. The active electrodes may comprise a pliable substrate with an electrically conductive adhesive. In an exemplary embodiment configured for frontal cortical stimulations, the active electrodes may be applied to the left and right mastoid region of the patient, with the reference electrode applied to the patient's forehead. However, it may be seen that in other configuration which may be optimized for other types of stimulation, the location, positioning, quantity, etc. of the active electrodes and the reference electrode(s) may be different.

The power supply, which in the exemplary embodiment may be optional and which may be a medical grade AC/DC power supply, may be any power supply or other which may be used to receive mains power and to permit that mains power to be conveyed the remainder of the system and utilized to ultimately produce a stimulation current. Likewise, the battery pack, which again may be an optional component, and which in the exemplary embodiment is a Ni-MH battery pack that also includes a battery management system, may serve to provide uninterrupted power during mains power failure, and which may serve to prevent artifact generation (spikes, jitters, etc.) that may occur during failure or intermittent losses or reduction in mains power delivery, as such artifacts may be included within the stimulation current which may result in inadvertent rectification of the stimulation by the skin and production of a DC current component, leading to patient discomfort. However, it may be seen that the presence or absence of these components are not of critical importance to the systems or methods herein disclosed, and that, such systems or methods may be performed without a battery pack or a power supply, so long as the mains power or other source of current used to produce the stimulation current is sufficient to enable performance of the herein discussed methods.

Figure 7:
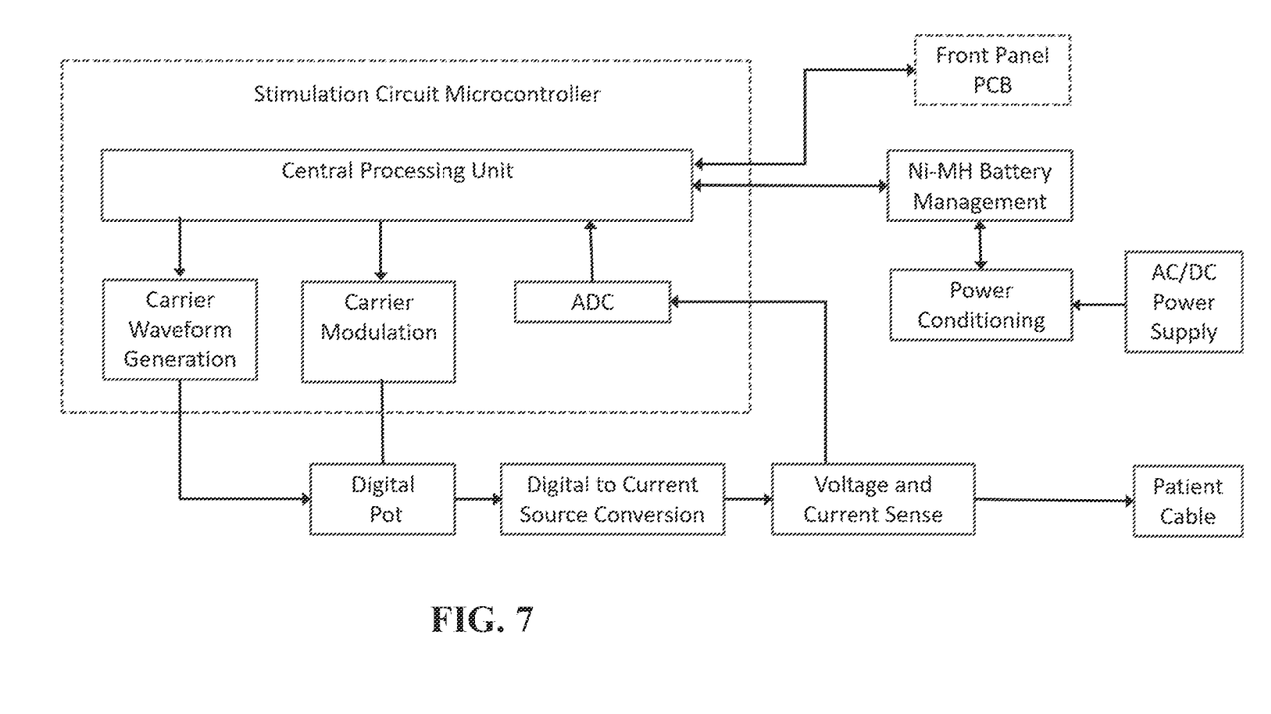
FIG. 7 is a block diagram showing, in greater detail, certain hardware and/or software components of a stimulation circuitry PCB included in one embodiment of a transcranial electrostimulation system for treating a patient for Alzheimer's Dementia.

Turning now to FIG. 7, a block diagram showing, in greater detail, certain hardware and/or software components of a stimulation circuitry PCB according to one embodiment of a transcranial electrostimulation system for treating a patient for Alzheimer's Dementia. As may be seen, the stimulation circuitry PCB may, in the exemplary embodiment shown, include a stimulation circuit microcontroller comprising a central processing unit (CPU), a waveform generator module, a waveform modulation module, and an analog to digital converter (ADC) module, with the stimulation circuitry PBC also including a digital to current source converter module, a voltage and current sense module, a digital potentiometer (pot), a Ni-MH battery management module, a power conditioning module, and inputs/outputs to the front panel PCB and to the patient cable. While this specific block diagram shows one exemplary version of the stimulation circuitry of a TACS system, it is certainly not the only configuration in which the systems and methods herein described may be achieved, and indeed, these descriptions of the physical and/or digital architecture of the stimulation circuitry of a TACS system are to be understood as being purely for exemplary purposes in order to enable the reader to more fully understand the nature of the herein described systems and methods, and are not to be interpreted as representing or imposing any limitations of the subject matter described herein. It is also to be understood that the respective modules described herein may be implemented in hardware, in software, or in combinations of hardware and software, including as subsidiary components of one another or integrated together.

The CPU may provide software control of all hardware functions in the TACS system. The CPU may also receive inputs from the ADC module and perform calculations based upon those inputs in order to control the functionality of the TACS system and its subordinate components in real time.

The carrier waveform generator module may be controlled by the CPU and may generate a carrier waveform according to the specific parameters desired, which may include a duty cycle and current amplitude ratio. The carrier waveform may then be then amplitude modulated with a carrier waveform via a digital potentiometer controlled by a waveform modulation model (also potentially controlled by the CPU) to perform the herein described steps in order to produce a digital representation of the herein described stimulation current. According to a preferred embodiment, the carrier waveform and thus the resulting stimulation current has a frequency of about 100 KHz.

Following amplitude modulation of the carrier waveform, a digital to current source converter, i.e., the stimulation current generator, may be used to ultimately generate, from a digital representation of the amplitude modulated carrier waveform, the actual stimulation current for subsequent delivery to the patient. According to a preferred embodiment, the stimulation current is about 15 mA. However, it may be seen that the stimulation current flow may also be at different rates.

The ADC module may be configured to receive analog information from a voltage and current sense module and to convert that analog information to digital information for use by the CPU in order to permit real-time adjustment of the stimulation current. Such analog information may be, according to certain contemplated embodiments, information received from an active electrode or a reference electrode, which may concern quality of electrode contact, electrical impedance, etc. Such information may be used to provide feedback to the CPU and to permit dynamic adjustments to be made in real time to the stimulation current, such as via adjustment of the underlying waveform, the modulation signal(s), or directly at the stimulation current itself.

In the exemplary embodiment, a power conditioning module may also be included within or in relation to the stimulation circuitry PCB for regulating the power supply to voltage supply rails for the operation of the microcontroller and the stimulation output circuitry.

Figure 8:
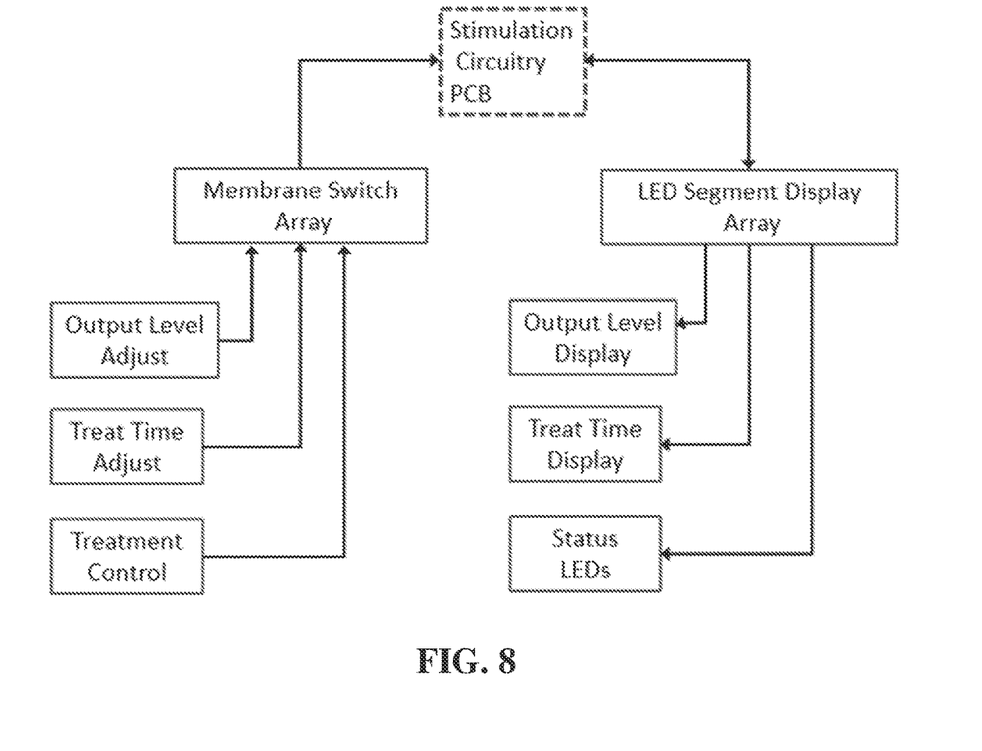
FIG. 8 is a block diagram showing certain hardware and/or software components of a front panel of an embodiment of a transcranial electrostimulation system for treating a patient for Alzheimer's Dementia.

Turning now to FIG. 8, a block diagram is illustrated that shows certain hardware and/or software components of a front panel of an exemplary embodiment of a transcranial electrostimulation system for treating a patient for Alzheimer's Dementia. In this exemplary embodiment, the front panel may be seen to include a membrane array switch and a LED segment display array. The membrane array switch may be utilized by the user of the TECS system in order to manually input adjustments to the parameters of the stimulation current, such as output level, treatment time, or treatment controls. The LED segment display array may be viewed by the user to visually confirm these parameters and the overall status of the device. It is to be understood that a this description of a front panel is purely illustrative in nature and is specific to one exemplary embodiment of a TECS system, and that the presence, absence, or specific configuration of any front panel, or any panel located anywhere on any such device, or the controls or displays contained therein, are purely illustrative of merely one particular embodiment, and these descriptions are certainly not meant to impose any limitations on the inventive aspects of the herein described systems and methods.

Figure 9:
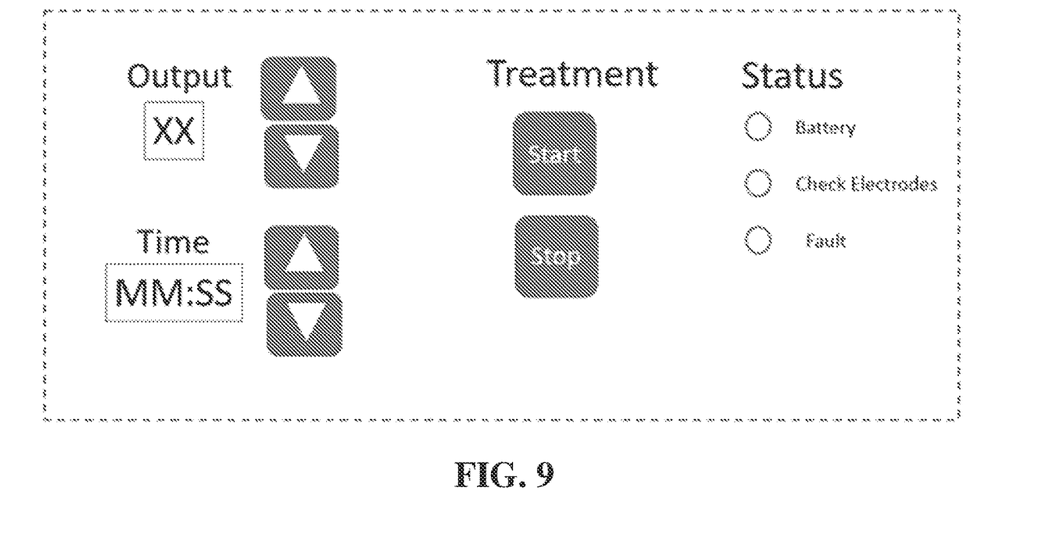
FIG. 9 is an exemplary image of a front panel user interface of an embodiment of a transcranial electrostimulation system for treating a patient for Alzheimer's Dementia.

Turning now to FIG. 9, an exemplary image of a front panel user interface of an embodiment of a transcranial electrostimulation system for treating a patient for Alzheimer's Dementia is shown. It may be seen that the front panel user interface may, according to the particular embodiment illustrated, include controls from adjusting an output, which may be a current level setpoint (i.e., in milliamperes) or even an alphanumeric signifier that relates to a treatment type, such as the output of a stimulation current according to one of the many aforementioned variations in frequency or multiple frequencies, or an entire set of predefined treatment parameters encompassed within a treatment modality. A treatment time may also be adjusted, as well as a manual start/stop button for beginning or ending the treatment. The front panel user interface may also contain, without limitation, one or more status LEDs for indicating a status condition, such as a battery status (i.e., fully charged, low charge, no charge remaining, etc.), a check electrode status (i.e., no or poor contact of one or more electrodes), or a general fault status which may indicate other conditions not encompassed by other status indicators. However, it is to be understood that a this description of a front panel user interface is purely illustrative in nature and is specific to one exemplary embodiment of a TECS system, and that the presence, absence, or specific configuration of any front panel user interface, or the controls or displays contained thereon or therein, are purely illustrative of merely one particular embodiment, and these descriptions are certainly not meant to impose any limitations on the inventive aspects of the herein described systems and methods.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A method for treating a patient for Alzheimer's Dementia, the method comprising:
generating a carrier waveform, the carrier waveform being an alternating current having a duty cycle ratio and a current amplitude ratio wherein portions of the carrier waveform that define a first polarity have greater magnitude and shorter duration than portions of the carrier waveform that define a second polarity opposite the first polarity, the duty cycle ratio and the current amplitude ratio being selected such that each respective pair of integrations of the current amplitude between successive time instances at which the carrier waveform alternates polarity is substantially equivalent despite a difference in magnitude between the portions of the carrier waveform defining the first and second polarities;
generating a stimulation current from the carrier waveform via amplitude modulating the carrier waveform, the extremes of the stimulation current defining a stimulation current envelope;
applying the stimulation current to the occipital region of the brain of the patient;
measuring the stimulation current at the patient;
determining an electrode contact impedance from the measured stimulation current; and
dynamically adjusting one or more parameters in real time with the generation of the stimulation current based upon the determined electrode contact impedance, the one or more parameters being one or more parameters of: the generated carrier waveform, the generated stimulation current, or combinations thereof.

2. The method of claim 1, wherein the extremes of the current envelope define a first series of pulses occurring at a first frequency.

3. The method of claim 2, wherein the first series of pulses occur at a frequency of about 40 Hz.

4. The method of claim 2, wherein the first series of pulses occur at a frequency of about 77.5 Hz.

5. The method of claim 2, wherein the first series of pulses occur at a frequency of about 4 Hz.

6. The method of claim 1, wherein the stimulation current is generated via amplitude modulating the carrier waveform such that the stimulation current envelope current further defines a second series of pulses occurring at a second frequency.

7. The method of claim 6, wherein the second series of pulses occur at a frequency selected from: about 4 Hz, about 40 Hz, about 77.5 Hz.

8. The method of claim 6, wherein said applying the stimulation current comprises applying the stimulation current to the occipital region of the brain of the patient for a treatment duration, wherein the first series of pulses occurs at a frequency of about 40 Hz for the entire treatment duration, and wherein the second series of pulses occurs at frequency of about 4 Hz for a first portion of the treatment duration, a frequency of about 40 Hz for a second portion of the treatment duration, and a frequency of about 77.5 Hz for a third portion of the treatment duration.

9. The method of claim 8, wherein the treatment duration is about an hour, and wherein each of the first portion of the treatment duration, the second portion of the treatment duration, and the third portion of the treatment duration is about 20 minutes.

10. The method of claim 1, wherein the stimulation current is generated via amplitude modulating the carrier waveform such that the stimulation current envelope defines a plurality of series of pulses, each respective one of the plurality of series of pulses occurring at a respective frequency.

11. The method of claim 10, wherein each of the plurality of stimulation current envelopes has a frequency selected from one or more of: about 4 Hz, about 40 Hz, about 77.5 Hz.

12. The method of claim 1, wherein the carrier waveform has a frequency of about 100 KHz.

13. The method of claim 1, wherein the carrier waveform is a rectangular wave.

14. The method of claim 1, wherein the stimulation current is generated so as to produce an uninterrupted non-zero resultant rectified charge.

15. A method of generating a stimulation current, the method comprising:
generating a carrier waveform, the carrier waveform being a rectangular alternating current having a first duty cycle ratio and a first current amplitude ratio wherein portions of the carrier waveform that define a first polarity have greater magnitude and shorter duration than portions of the carrier waveform that define a second polarity opposite the first polarity, the first duty cycle ratio and the first current amplitude ratio being selected such that each respective pair of integrations of the current amplitude between successive time instances at which the waveform alternates polarity is substantially equivalent despite a difference in magnitude between the portions of the carrier waveform defining the first and second polarities;
amplitude modulating the carrier waveform to derive a stimulation current, the extremes of the stimulation current defining a stimulation current envelope;
determining an electrode contact impedance from a measured stimulation current; and
dynamically adjusting one or more parameters in real time with the generation of the stimulation current based upon the determined electrode contact impedance, the one or more parameters being one or more parameters of: the generated carrier waveform, the generated stimulation current, or combinations thereof.

16. A method for treating a patient for Alzheimer's Dementia, the method comprising:
generating a carrier waveform, the carrier waveform being an alternating current having a duty cycle ratio and a current amplitude ratio wherein portions of the carrier waveform that define a first polarity have greater magnitude and shorter duration than portions of the carrier waveform that define a second polarity opposite the first polarity, the duty cycle ratio and the current amplitude ratio being selected such that each respective pair of integrations of the current amplitude between successive time instances at which the carrier waveform alternates polarity is substantially equivalent despite a difference in magnitude between the portions of the carrier waveform defining the first and second polarities;
generating a stimulation current from the carrier waveform via amplitude modulating the carrier waveform, the extremes of the stimulation current defining a stimulation current envelope;
applying the stimulation current to the occipital region of the brain of the patient;
measuring the stimulation current at the patient;

determining an electrode contact impedance from the measured stimulation current; and dynamically adjusting one or more parameters in real time with the generation of the stimulation current based upon the determined electrode contact impedance, the one or more parameters being one or more parameters of: the generated carrier waveform, the generated stimulation current, or combinations thereof.

17. The method of claim 16, wherein the extremes of the current envelope define a first series of pulses occurring at a first frequency.

18. The method of claim 17, wherein the first series of pulses occur at a frequency of about 40 Hz.

19. The method of claim 17, wherein the first series of pulses occur at a frequency of about 77.5 Hz.

20. The method of claim 17, wherein the first series of pulses occur at a frequency of about 4 Hz.

\* \* \* \* \*